(12) United States Patent
Kapit

(10) Patent No.: US 6,296,482 B1
(45) Date of Patent: Oct. 2, 2001

(54) ORTHODONTIC HEIGHT POSITIONING GAUGE WITH ROTATABLE HEADS

(76) Inventor: Arthur L. Kapit, 18064 Sentinel Cir., Boca Raton, FL (US) 33496

( * ) Notice: Subject to any disclaimer, the term of this patent is extended or adjusted under 35 U.S.C. 154(b) by 0 days.

(21) Appl. No.: 09/746,444

(22) Filed: Dec. 26, 2000

(51) Int. Cl.[7] .................................................. A61C 3/00
(52) U.S. Cl. ............................................................... 433/3
(58) Field of Search ................................. 433/3, 4, 141

(56) References Cited

U.S. PATENT DOCUMENTS

| | | | |
|---|---|---|---|
| 2,290,482 | 7/1942 | Neil | 433/72 |
| 3,871,098 | * 3/1975 | Dean | 433/3 |
| 4,273,532 | 6/1981 | Hass | 433/37 |
| 4,959,014 | 9/1990 | Sheridan | 433/72 |
| 5,312,248 | * 5/1994 | Zandkarimi | 433/3 |
| 5,876,204 | 3/1999 | Day et al. | 433/173 |

* cited by examiner

Primary Examiner—John J. Wilson
(74) Attorney, Agent, or Firm—Gregory J. Gore

(57) ABSTRACT

An orthodontic height hand gauge is both double-ended and double-sided, allowing four measurement heights to be determined by a single tool. Each end of the gauge has a rotatable element capable of rotating and stopping at zero degrees, 45 degrees, and 90 degrees from the handle axis by a plunger mechanism which provides a detent function. Rotatable ends provide proper gauge alignment to the tooth, especially for difficult-to-reach teeth in the back of the mouth. A center tab extends longitudinally from each rotatable element and is separated by a given distance from top and bottom legs which extend parallel to the center tab. The distances between the center tab and the legs are two different gauge heights to be measured. Thus, by using both ends of the tool, four gauge distances can be measured.

7 Claims, 1 Drawing Sheet

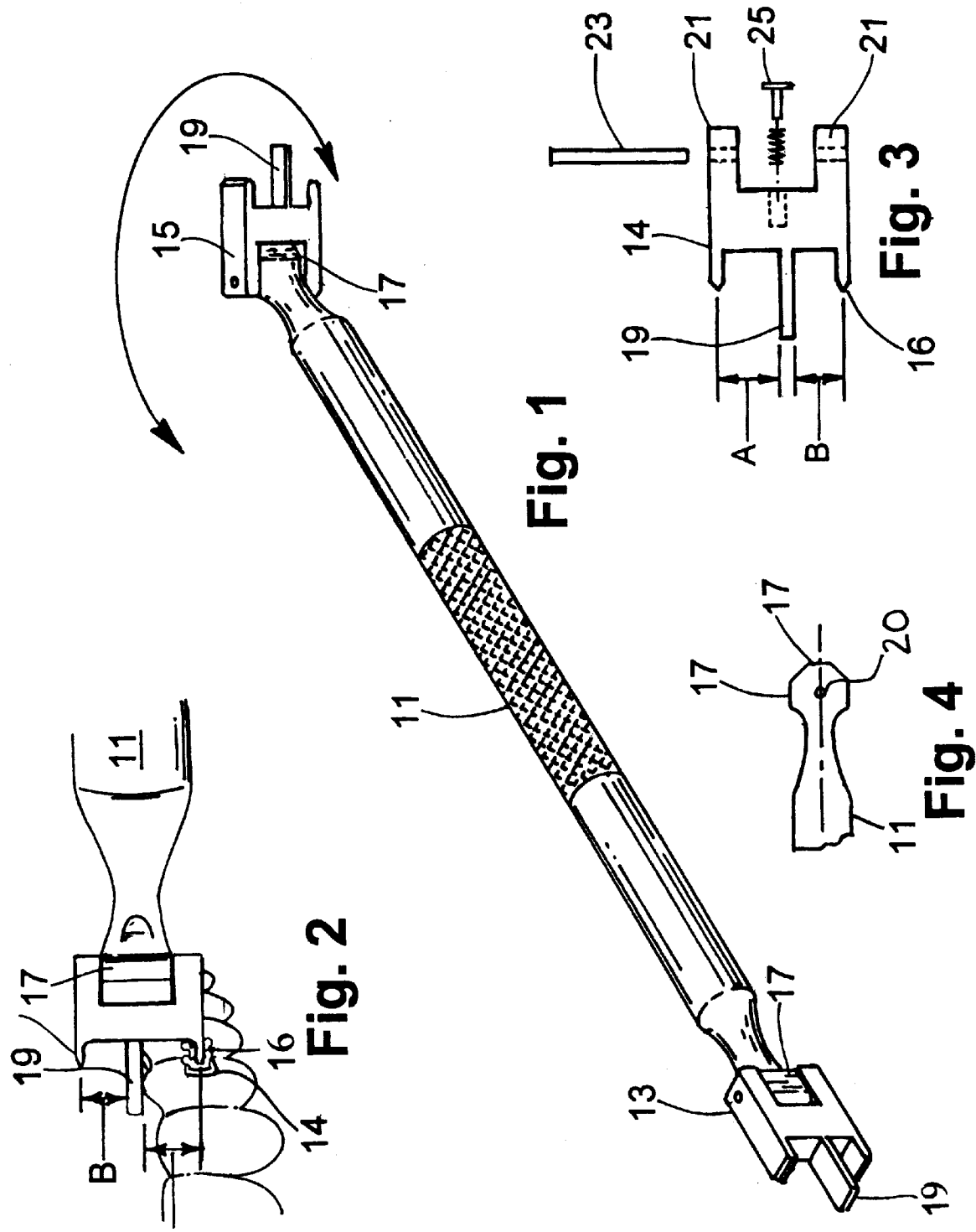

ORTHODONTIC HEIGHT POSITIONING GAUGE WITH ROTATABLE HEADS

FIELD OF THE INVENTION

The present invention relates to an intra oral measurement device for the placement of orthodontic brackets, bands or tubes used in dentistry. More specifically, it relates to the placement of intraoral orthodontic appliances a specific distance from the occlusal or incisal edge of a tooth.

BACKGROUND OF THE INVENTION

This invention relates generally to placement of orthodontic brackets, bands or tubes at a specific distance from the occlusal or incisal edge of the tooth. The process for placement of brackets to the teeth includes first placing an adhesive on the underside of the orthodontic bracket. Next, the bracket is placed in the mouth with a tweezer-like instrument onto the tooth. Once placed on the tooth the bracket is positioned approximately in the center of the tooth from the front to back of the tooth and approximately in the center from gum tissue to the top edge of the tooth. More accurate placement is provided by the use of a height gauge which is placed on the top edge of the tooth. The bracket is then moved to a point where an element of the gauge fits into the bracket slot. This places the bracket at the correct height which in standard practice is precisely 3.5, 4.0, 4.5 or 5.0 mm from the top of the tooth.

Problems exist with prior art gauges because the instrument cannot be placed perpendicular to the buccal surface with any degree of comfort to the patient. This is because prior art gauges are rigid, unitary, elongate instruments which are difficult to fit into a patient's mouth at the proper angle with the tooth to which the bracket is to be affixed. The cheek prevents the instrument from being positioned properly. Inaccurate placement of the orthodontic attachments directly affects the ultimate position of the teeth and results in a poor final treatment result. Poorly placed brackets will result in height differentials and teeth that are malaligned in the vertical dimension.

SUMMARY OF THE INVENTION

The present invention has been devised to overcome the problems in the orthodontic dental arts described above. The present invention is an orthodontic attachment height gauge that is double-ended and double-sided allowing all four measuring heights be contained in one instrument. Each end of the gauge is a moveable element capable of rotating and stopping (via a plunger mechanism which exerts pressure on the hexagonal shaped non-working portion of the shaft) at 0–45–90 degrees in either direction. This unique feature allows the instrument to pass into the mouth along the inside of the cheek and be positioned properly to measure the teeth. From the front of the mouth the instrument is set at 0 degrees for the anterior teeth. Along the side it can be rotated to 45 degrees and for the molars in back of the mouth to 90 degrees while held perpendicular to the long axis of the tooth to be measured. The low profile enables it to fit comfortably between the teeth and cheek. The center portion of the working element is placed on the occlusal/incisal surface of the teeth and the orthodontist chooses the height to be used and places the appropriate male extrusion in the bracket slot to accurately position the orthodontic attachment.

More specifically, it allows the orthodontist to place the orthodontic attachments at precisely 3.5, 4.0, 4.5, 5.0 mm from the top of the tooth with accuracy and patient comfort.

In the preferred embodiment of the invention, the height measuring gauge allows that all four heights are contained in one gauge and each end of the instrument is able to rotate to 45 and 90 degrees in either direction which allows access to the posterior teeth choosing any of the four heights.

It is therefore the object of the present invention to provide a multiple height orthodontic gauge in one instrument. It is a further object to provide a height gauge instrument that can accurately place orthodontic appliances with patient comfort. Other objects and advantages of the invention will be apparent from the following drawings and description of the preferred embodiment.

BRIEF DESCRIPTION OF THE DRAWINGS

FIG. 1 is a top right front isometric view of the present invention.

FIG. 2 is a side view showing the present invention in use.

FIG. 3 is an assembly side view of a measuring head and detent means..

FIG. 4 is a top view of the end of the tool handle.

DESCRIPTION OF THE PREFERRED EMBODIMENT

Referring now to FIG. 1, the hand held dental instrument of the present invention is shown which includes a knurled handle 11 centrally located on an elongate main body. Rotatable measuring heads 13 and 15 are located at opposite ends of the handle. Each head is rotatable about a pinned hinge, the heads may be rotated through a 180 degree arc and the instrument handle may be rotated axially 180 degrees so that a top or bottom portion of each head may be used as further described herein. Gauge tabs 19 extend from the heads which are rotatably affixed to the ends of the handle by a yoke and hinge mechanism. Each head includes a yoke and a hinge. The distal ends of the handle has flat portions 17 which cooperate with a spring-biased pin in the center of each yoke to supply a detent function which holds each head in a position of straight axial alignment or positions 45 and 90 degrees on either side of the longitudinal axis. Greater detail of each head's yoke and detent mechanism is shown in FIGS. 3 and 4.

Referring now to FIG. 2, the present invention is shown in use. The critical measurement distance is between the gauge tab 19 and a bracket positioning leg 18 spaced a proscribed distance from the tab. As previously stated, each head of the present invention includes two different spacings between the center tab and the legs on either side of the center tab so that a total of four spacings can be provided in one tool. As shown in FIG. 2, the tab 19 is placed against the end of a tooth and a leg 18 is inserted into the orthodontic bracket slot 14 to be positioned on the face of the tooth. This will position the bracket the distance "A" from the end of the tooth. It should be readily understood that by rotating the tool radially 180 degrees, the opposing portion of the same head may be used to measure a second distance "B" in the same manner. As shown in FIG. 1, a second head is found on the opposite end of the instrument which functions in exactly the same manner except that the distances between the positioning legs and the center tab are different than the distances "A" and "B" of the first head, thus providing four different measurement distances in one device. These distances are preferable 3.5, 4.0, 4.5 and 5.0 millimeters. Each head is rotatable about handle 11 so that either head may be properly positioned orthogonal to the line of the tooth which the handle is positioned at a comfortable angle within the patient's mouth. This is particularly advantageous when positioning brackets on molars in the rear of the patient's mouth. Flat surfaces 17 provide a detent function as further described below.

Referring now to FIG. 3, greater detail of the rotatable heads is shown. As previously described, each head includes a center tab 19 and top and bottom legs 14 and 16 which are spaced at different distances from the center tab. Each head includes a yoke with arms 21 with means to receive a hinge pin 23. Each yoke further includes a spring-biased plunger which cooperates with flat surfaces 17 on the ends of the instrument handle 11 shown in FIG. 4 to hold the head in either an axially straight or deflected position depending upon how the handle is positioned in the patient's mouth. As shown in FIG. 4, the end of the handle includes aperture 20 for receiving the hinge pin. In this embodiment the structures at the end of the instrument handle are flats which contact a flat head of the plunger which is biased outwardly by a spring. It will be understood by those of ordinary skill in the art that other commonly used detent mechanisms such as resiliently captivated balls and cooperating sockets may also be used.

From the foregoing description of the preferred embodiment it should be readily apparent that the objects of the dental instrument of the present invention have been achieved. This single tool provides the ability to accurately measure four different bracket positioning distances. The rotatable heads provide not only for accuracy but also patient comfort. It should be understood that there may be other modifications and changes to the present invention that will be obvious to those of skill in the art from the foregoing description, however, the present invention should be limited only by the following claims and their legal equivalents.

What is claimed is:

1. A hand-held dental instrument comprising:
an elongate handle having a rotatable head at a first end;
a tab longitudinally extending from the center of said head; and
an orthodontic bracket positioning leg extending longitudinally from said head, said leg being parallel to said tab and spaced a gauge distance from a first side of said tab.

2. The hand-held dental instrument of claim 1 further including a second orthodontic bracket positioning leg longitudinally extending from said head, said leg spaced a second gauge distance from an opposite side of said center tab.

3. The dental instrument of claim 2 wherein the second gauge distance is different from said first gauge distance.

4. The hand-held dental instrument of claim 3 wherein said head includes a yoke and hinge means for rotatably affixing said head to said handle.

5. The dental instrument of claim 4 wherein said yoke includes detent means for releasably holding said head at an angle with respect to said handle.

6. The dental instrument of claim 5 wherein the dentent means includes a spring-biased plunger located between opposing arms of said yoke, whereby said plunger forceably contacts positioning means on the end of said handle.

7. The dental instrument of claim 6 further including a second rotatable head located on an opposite end of said handle from said first rotatable head, said second head being of substantially identical construction as said first head except that the gauge distances of the second head includes third and fourth gauge distances which are different than said first and second gauge distances.

* * * * *